US007083769B2

(12) United States Patent
Moerters et al.

(10) Patent No.: US 7,083,769 B2
(45) Date of Patent: Aug. 1, 2006

(54) SILICON-TITANIUM MIXED OXIDE POWDER PREPARED BY FLAME HYDROLYSIS, WHICH IS SURFACE-ENRICHED WITH SILICON DIOXIDE, AND THE PREPARATION AND THE USE THEREOF

(75) Inventors: Martin Moerters, Hanau (DE); Ina Hemme, Hanau (DE); Steffen Hasenzahl, Hanau (DE); Uwe Diener, Grosskrotzenburg (DE); Herbert Habermann, Biebergemuend (DE)

(73) Assignee: Degussa AG, Duesseldorf (DE)

( * ) Notice: Subject to any disclaimer, the term of this patent is extended or adjusted under 35 U.S.C. 154(b) by 132 days.

(21) Appl. No.: 10/326,554

(22) Filed: Dec. 23, 2002

(65) Prior Publication Data
US 2003/0129153 A1    Jul. 10, 2003

(30) Foreign Application Priority Data
Dec. 22, 2001   (DE)  ............................... 101 63 938

(51) Int. Cl.
*C01B 33/20* (2006.01)
*A61Q 17/04* (2006.01)
(52) U.S. Cl. ..................... 423/326; 423/598; 428/404; 424/59; 424/489; 424/724
(58) Field of Classification Search ............... 423/326, 423/598; 428/402, 404; 424/489, 59, 724
See application file for complete search history.

(56) References Cited

U.S. PATENT DOCUMENTS 5,451,390 A    9/1995    Hartmann et al.

FOREIGN PATENT DOCUMENTS

| DE | 36 11 449 | 10/1987 |
| DE | 42 35 996 | 4/1994 |
| EP | 0 988 853 | 3/2000 |

OTHER PUBLICATIONS

Patent Abstracts of Europe, EP 1 256 550, Nov. 13, 2002.
Patent Abstracts of Japan, JP 07-041315, Feb. 10, 1995.
Technical data'sof Admatechs K. K., "Titania-Silica Composite Oxide", 2 pages.
Patent Abstracts of Japan, JP 63-045123, Feb. 26, 1988.

(Continued)

*Primary Examiner*—David Sample
(74) *Attorney, Agent, or Firm*—Oblon, Spivak, McClelland, Maier & Neustadt, P.C.

(57) ABSTRACT

Silicon-titanium mixed oxide powder prepared by flame hydrolysis, having a ratio by weight of silicon dioxide/titanium dioxide, which is greater on the surface of the primary particles than that within the total primary particle. It is prepared by a flame hydrolysis process, in that a stream consisting of a vaporous titanium dioxide precursor and oxygen or an oxygen-containing gas and hydrogen, and a second stream consisting of a vaporous silicon dioxide precursor and a carrier gas consisting of oxygen, an oxygen-containing gas and/or an inert gas, are guided separately into the reaction chamber of a burner such as is known for the preparation of pyrogenic oxides, and are burnt here, the solid mixed oxide powder and hot gases are subsequently cooled, and the gases are separated from the solid. The powder may be used, for example, for the preparation of sunscreen preparations.

23 Claims, 1 Drawing Sheet

OTHER PUBLICATIONS

A. T. Liu, et al., Novel Ceramic Fabrication Processes and Applications, pp. 1-10, XP-001179377, "Production of Fumed Oxides by Flame Hydrolysis", 1986.

C.-H. Hung, et al., Journal of Materials Research, vol. 7, No. 7, pp. 1861-1869, XP-009025974, "Formation of Mixed Oxide Powders in Flames: Part I. $TiO_2$-$SiO_2$", Jul. 1992.

Nicholas J. Lowe, et al., "Sunscreens Development, Evaluation, and Regualatory Aspects", Cosmetic Science and Technology, vol. 10, pp. 211-266.

Andreas Domsch., "Die kosmeticschen Präparate", Verlag für chemische Industrie (Ed. H. Ziolkowsky), 4th Edition, 1992, pp. 446-469.

10 nm

SILICON-TITANIUM MIXED OXIDE POWDER PREPARED BY FLAME HYDROLYSIS, WHICH IS SURFACE-ENRICHED WITH SILICON DIOXIDE, AND THE PREPARATION AND THE USE THEREOF

BACKGROUND OF THE INVENTION

1. Field of the Invention

The present invention relates to silicon-titanium mixed oxide powder prepared by flame hydrolysis, which is surface-enriched with silicon dioxide, and the preparation and use thereof.

2. Description of the Background

Titanium dioxide is widely used in sunscreen preparations. Its action substantially resides in the reflection, scattering and absorption of damaging UV radiation and is substantially dependent on the primary particle size of the metal oxides.

A disadvantage here is its photocatalytic activity, which triggers reactions which may give rise to changes in the constituents of a sunscreen preparation.

In an attempt to reduce the photocatalytic activity without diminishing the UV-screening properties, titanium dioxide is, for example, enclosed in a silicon dioxide shell.

The need for two reaction steps, with the correspondingly high capital cost, to prepare such enclosed particles is a disadvantage. The two steps incorporate the preparation of the titanium dioxide particles and the formation of the shell, generally in an aqueous (U.S. Pat. No. 6,773,814) or aqueous-alcoholic (U.S. Pat. No. 6,235,270) medium by the hydrolysis of a silicon dioxide precursor.

U.S. Pat. No. 5,451,390 describes a silicon-titanium mixed oxide prepared by flame hydrolysis and the use thereof as a UV-absorber in sunscreen preparations. Although this powder can be prepared in a single reaction step, the photoctalytic activity, in relation to titanium dioxide prepared by flame hydrolysis, is reduced to a lesser degree than is the case when titanium dioxide is enclosed in silicone dioxide.

Accordingly, there remains a need for a material which overcomes these disadvantages.

SUMMARY OF THE INVENTION

It is an object of the invention to provide a powder which avoids the disadvantages of the prior art. Such a powder should, in particular, have a low photocatalytic activity and be simple to prepare.

Thus, the present invention provides a silicon-titanium mixed oxide power prepared by flame hydrolysis, where the ratio by weight of silicon dioxide/titanium dioxide on the surface of the primary particles is greater than that within the total primary particle.

The present invention also provides a process for the preparation of the powder described above, comprising:

guiding separately into the reaction chamber of a burner a first stream consisting of a vaporous titanium dioxide precursor and oxygen or an oxygen-containing gas and hydrogen, and a second stream consisting of a vaporous silicon dioxide precursor and a carrier gas consisting of oxygen, an oxygen-containing gas and/or an inert gas, burning the first and second stream in the reaction chamber of the burner, cooling the solid mixed oxide powder and hot gases, and separating the gases from the solid.

The present invention also provides composition containing the powder described above, especially a sunscreen preparation.

A more complete appreciation of the invention and many of the attendant advantages thereof will be readily obtained as the same becomes better understood by reference to the following Figures in conjunction with the detailed description below.

DETAILED DESCRIPTION OF THE INVENTION

Figure 1:
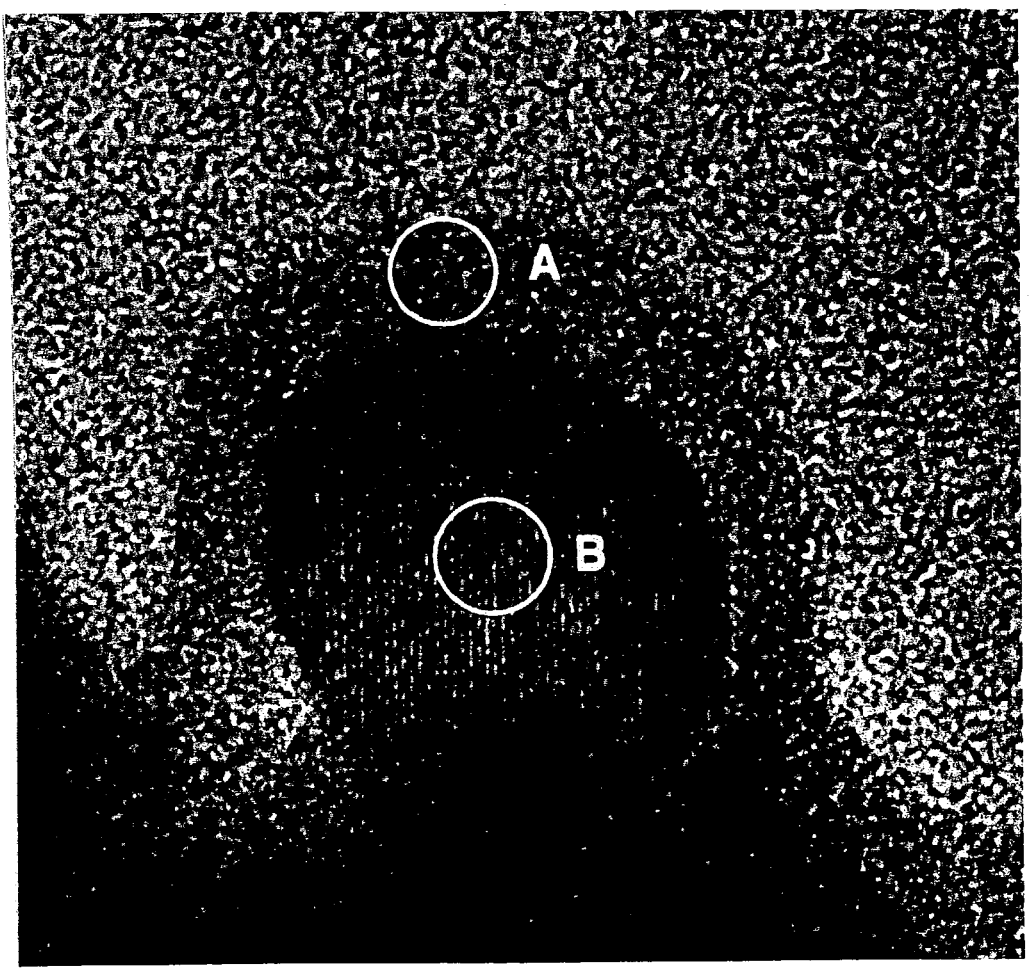
FIG. 1: TEM image of the powder produced in Example 1 herein.

The ratio by weight of silicon dioxide/titanium dioxide on the surface can be determined by, for example, X-ray-induced photoelectron spectroscopy (XPS analysis) of the powder. Additional information relating to the surface composition can be determined by energy-dispersive X-ray analysis (TEM-EDX analysis) of individual primary particles.

The ratio by weight within the total primary particle is determined by chemical or physico-chemical methods, for example X-ray fluorescence analysis of the powder. The total primary particle also includes the proportion of silicon dioxide and titanium dioxide on the surface. It is the particle which is formed initially in the flame hydrolysis process. The primary particles are able in the further course of the reaction to grow together into chain-like aggregates, in turn forming agglomerates. Depending on the reaction conditions selected, substantially spherical particles can also be obtained in the synthesis.

Mixed oxide is understood to be the intimate mixture of titanium dioxide and silicon dioxide on an atomic level, with the formation of Si—O—Ti bonds. The primary particles may, in addition, also have regions of silicon dioxide as well as titanium dioxide.

The silicon-titanium mixed oxide powder according to the invention may furthermore contain traces of impurities from the starting materials, as well as also impurities resulting from the process. These impurities may amount to up to 0.5 wt. %, however generally not more than 100 ppm.

The ratio by weight of $SiO_2/TiO_2$, in relation to the total primary particle, may be from 0.01 to 99 in the powder according to the invention. This range includes all specific values and subranges therebetween, such as 0.02, 0.05, 0.1, 0.2, 0.5, 1, 2, 5, 10, 25, 50, 75, 80, 90, 95, 97, and 98. Within this range the ratio by weight of silicon dioxide/titanium dioxide on the surface of the primary particles is greater than that within the total primary particle.

Provided that the ratio by weight of $SiO_2/TiO_2$ is between 0.05 and 4, in relation to the total primary particle, in a particular embodiment the ratio by weight of $SiO_2/TiO_2$ on the surface of the primary particle can assume a value which can be calculated from the formula:

$$[SiO_2/TiO_2]_{surface} = 9.3 [SiO_2/TiO_2]_{total\ primary\ particle}^{1.24},$$

with the maximum absolute deviation of the ratio by weight of $[SiO_2/TiO_2]$surface from the indicated formula being 1.5.

For instance, an $SiO_2/TiO_2$ ratio of 0.1 within the total primary particle corresponds to a surface ratio of 0.64. The experimentally determined value is around 0.57, and the absolute deviation is accordingly 0.07 (q.v. Example 2).

The powder according to the invention can have BET surface areas of between 10 and 300 m²/g. This range includes all specific values and subranges therebetween, such as 25, 50, 75, 100, 150, 200, and 250 m²/g. The BET surface area may be varied within a specified range by means of the process parameters. The ratio by weight of $SiO_2/TiO_2$ furthermore exerts an influence on the BET surface area. With the process parameters unchanged, a greater BET surface area will be achievable more easily when the $SiO_2/TiO_2$ ratio is increased.

The present invention also provides a process for the preparation of the silicon-titanium mixed oxide powder according to the invention. Here, a stream consisting of a vaporous titanium dioxide precursor and oxygen or an oxygen-containing gas and hydrogen, and a second stream consisting of a vaporous silicon dioxide precursor and a carrier gas consisting of oxygen, an oxygen-containing gas and/or an inert gas, are guided separately into the reaction chamber of a burner such as is known for the preparation of pyrogenic oxides, where the mixture burns, the solid mixed oxide powder and hot gases are then cooled, and the gases are separated from the solid.

The mixture consisting of the silicon dioxide precursor and the carrier gas may be supplied at one or more positions in the reaction chamber. The mixed oxide powder may optionally be purified by means of a heat treatment by means of gases humidified with water vapour.

Inorganic and/or organic compounds may be utilized as the titanium dioxide precursor and silicon dioxide precursor. Halides are particularly suitable as inorganic compounds. Siloxanes such as hexamethyl disiloxane are particularly suitable as organic compounds. Silicon tetrachloride and titanium tetrachloride are particularly suitable.

In a particular embodiment, titanium tetrachloride can be introduced as the titanium oxide precursor and silicon tetrachloride can be introduced as the silicon dioxide precursor, in a manner such that the ratio by weight of $SiO_2/TiO_2$ on the surface becomes adjusted by the ratio by weight of $SiCl_4/TiCl_4$ corresponding to the formula:

$$[SiO_2/TiO_2]_{surface}=7.3[SiCl_4/TiCl_4]^{1.28},$$

with a 1.5 maximum absolute deviation of the ratio by weight of $[SiO_2/TiO_2]$surface from the indicated formula, provided that the ratio by weight of $SiO_2/TiO_2$ in the subsequent powder is between 0.05 and 4, in relation to the total primary particle.

The present invention also provides sunscreen preparations that contain the mixed oxide powder according to the invention in a proportion of between 0.01 and 25 wt. %. The sunscreen preparation according to the invention can in addition be utilised in mixtures with known inorganic UV-absorbing pigments and/or chemical UV filters.

Titanium dioxides, zinc oxides, aluminium oxides, iron oxides, silicon dioxide, silicates, cerium oxides, zirconium oxides, barium sulfate or mixtures thereof are considered as known UV-absorbing pigments.

All water- or oil-soluble UVA and also UVB filters known to those skilled in the art are considered as chemical UV filters which might be exemplified by, but not limited to, sulfonic acid derivatives of benzophenones and benzimidazoles, derivatives of dibenzoyl methane, benzylidene camphors and derivatives thereof, derivatives of cinnamic acid and esters thereof, or esters of salicylic acid.

The sunscreen preparations according to the invention may furthermore contain the solvents known to those skilled in the art, such as water, monohydric or polyhydric alcohols, cosmetic oils, emulsifiers, stabilisers, consistency regulators such as carbomers, cellulose derivatives, xanthan gum, waxes, bentones, pyrogenic silicas and further substances which are conventional in cosmetics, such as vitamins, antioxidants, preservatives, dyes and perfumes.

The sunscreen preparation according to the invention may typically be present as an emulsion (O/W, W/O or multiple), aqueous or aqueous-alcoholic gel or oil gel and be supplied in the form of lotions, cremes, milk sprays, mousse, as a stick or in other common forms.

The general structure of sunscreen preparations is moreover described in A. Domsch, "Die kosmetischen Praparate", Verlag fur chemische Industrie (Ed. H. Ziolkowsky), 4th edition, 1992, incorporated herein by reference, or N. J. Lowe and N. A. Shaat, Sunscreens, Development, Evaluation and Regulatory Aspects, Marcel Dekker Inc., 1990, incorporated herein by reference.

The present invention also provides the use of the mixed oxide powders described herein as a UV filter, for the preparation of dispersions, in processes for chemical mechanical polishing (CMP use), in glass manufacture, as a catalytically active substance, as a catalyst support, for use in toners and as an additive in the silicone and rubber industry.

EXAMPLES

Having generally described this invention, a further understanding can be obtained by reference to certain specific examples which are provided herein for purposes of illustration only and are not intended to be limiting unless otherwise specified.

Example 1

0.688 kg/h $TiCl_4$ is volatilized in an evaporator at approx. 200° C., and the chloride vapour is passed by means of nitrogen into the mixing chamber of a burner. Here, the gas stream is mixed with 0.283 Nm³/h hydrogen and 0.837 Nm³/h dried air (=air stream 1). In a further evaporator 0.232 kg/h $SiCl_4$ is vaporised at approx. 100° C. and is guided into the burner by means of 0.763 Nm³/h dry air (=air stream 2).

The burner comprises three concentric tubes. The mixture of air and gaseous $SiCl_4$ is supplied to the flame through the inside tube (internal diameter 4 mm). The mixture of $TiCl_4$, air and hydrogen is supplied from the mixing chamber to the flame through the middle tube (diameter 7 mm). Consequently, at a burner temperature of 230° C., for both tubes exit velocities of approx. 35.8 m/s result. 0.05 Nm³/h hydrogen is supplied through the outside tube as a jacket-type gas.

The gases are burnt in the reaction chamber and are cooled to approx. 110° C. in a coagulation zone downstream. The resulting mixed oxide is then separated in a filter. Adherent chloride is removed by a treatment of the powder with humid air at approx. 500–700° C.

The resulting oxide powder has a ratio by weight of $SiO_2/TiO_2$ of 0.28. The BET surface area is 72 m²/g. High-resolution TEM images with EDX analysis show that the surface (position A in the Figure) has a ratio by weight of $SiO_2/TiO_2$ of 2 and is amorphous in character. The thickness of this layer is approx. 4 nm.

The TEM image of the powder prepared in accordance with Example 1 furthermore shows a crystalline core (position B in the Figure). EDX analysis shows that this comprises very largely titanium dioxide. A ratio of the titanium dioxide forms anatase/rutile of 80:20 can be detected by X-ray diffraction.

Examples 2–10

Further tests are conducted in accordance with the description provided in Example 1. Here, the ratio of $SiCl_4$/$TiCl_4$ and the gas quantities are varied in accordance with Table 1, resulting in the powder properties which are summarised in Table 2.

TABLE 1

Equiptment settings for Examples 1–10

| Example | $H_2$ via mixing-chamber $Nm^3/h$ | $H_2$ via jacket $Nm^3/h$ | Air-stream 1 $Nm^3/h$ | Air-stream 2 $Nm^3/h$ | $TiCl_4$ kg/h | $SiCl_4$ kg/h |
|---|---|---|---|---|---|---|
| 1 | 0.283 | 0.050 | 0.837 | 0.763 | 0.688 | 0.232 |
| 2 | 0.300 | 0.225 | 1.974 | 1.605 | 1.538 | 0.192 |
| 3 | 0.566 | 0.100 | 1.664 | 1.536 | 1.371 | 0.398 |
| 4 | 0.307 | 0.100 | 1.470 | 1.205 | 1.000 | 0.396 |
| 5 | 0.566 | 0.100 | 1.268 | 1.232 | 1.193 | 0.593 |
| 6 | 0.566 | 0.100 | 1.688 | 1.512 | 1.195 | 0.595 |
| 7 | 0.566 | 0.100 | 1.714 | 1.486 | 1.000 | 0.800 |
| 8 | 0.409 | 0.050 | 1.967 | 1.533 | 0.593 | 0.690 |
| 9 | 0.566 | 0.100 | 1.759 | 1.441 | 0.696 | 1.196 |
| 10 | 0.566 | 0.050 | 1.779 | 1.421 | 0.480 | 1.320 |

In all the experiments shown TEM-EDX analysis or XPS analysis indicates a pronounced enrichment of $SiO_2$ on the surface of the primary particles.

TABLE 2

Powder properties relating to Example 1–10:

| Example | BET-surface area $m^2/g$ | $SiO_2$/$TiO_2$ total particle | $SiO_2$/$TiO_2$ surface exp.(*) | $SiO_2$/$TiO_2$ surface calc. | Deviation exp./calc. absolute |
|---|---|---|---|---|---|
| 1 | 72 | 0.28 | 2.03 | 1.95 | 0.08 |
| 2 | 72 | 0.10 | 0.64 | 0.57 | 0.07 |
| 3 | 78 | 0.24 | 1.63 | 1.61 | 0.02 |
| 4 | 77 | 0.33 | 2.13 | 2.38 | 0.25 |
| 5 | 65 | 0.42 | 2.85 | 3.15 | 0.30 |
| 6 | 94 | 0.42 | 3.00 | 3.15 | 0.15 |
| 7 | 86 | 0.68 | 5.25 | 5.76 | 0.51 |
| 8 | 157 | 0.98 | 10.11 | 9.03 | 1.08 |
| 9 | 99 | 1.44 | 15.67 | 14.65 | 1.02 |
| 10 | 152 | 2.31 | 24.80 | 26.25 | 1.45 |

*determined by XPS analysis

Example 11

Comparison Example 1.331 kg/h $TiCl_4$ are volatilised in an evaporator at approx. 200° C., and 0.332 kg/h $SiCl_4$ is volatilised in a further evaporator at approx. 100° C. The chloride vapours are passed by means of nitrogen into the mixing chamber of a burner of a known design. Here, the gas stream is mixed with 0.182 $Nm^3/h$ hydrogen and 2.675 $Nm^3/h$ dried air. The gases are passed together into the reaction chamber and are burnt. The supporting flame (jacket) is here fed with 0.225 $Nm^3/h$ hydrogen. In a coagulation zone downstream the reaction products are cooled to approx. 110° C. The resulting mixed oxide is then separated in a filter. Adherent chloride is removed by a treatment of the powder with humid air at approx. 500–700° C.

The resulting oxide powder contains in total 17.3 wt. % $SiO_2$ and 82.7 wt. % $TiO_2$. The BET surface area is 51 $m^2/g$. TEM-EDX analysis shows no significant difference in concentration between the interior of the primary particles and the surface of the primary particles.

Example 12

Photocatalytic Activity

In order to determine the photocatalytic activity, the sample which is to be measured is suspended in 2-propanol and irradiated with UV light for 1 hour. The concentration of acetone formed is afterwards measured.

Approx. 250 mg (accuracy 0.1 mg) of the particles obtained from the Examples and Comparison Examples are suspended in 350 ml (275.1 g) 2-propanol in an Ultra-Turrax mixer. By way of a cooler temperature-controlled to 24° C. this suspension is transported by means of a pump into a glass photoreactor having a radiation source, which is previously purged with oxygen.

A medium-pressure Hg submersible lamp of the TQ718 type (Heracus) with a 500 W output, for example, serves as the radiation source. A borosilicate glass protective tube limits radiation emission to wavelengths of >300 nm. The radiation source should be surrounded externally by a cooling tube with water through-flow. Oxygen is dispensed into the reactor by way of a flowmeter. The reaction is initiated when the radiation source is switched on. A small amount of the suspension is removed as soon as the reaction ends, is filtered and is analysed by gas chromatography.

Example 3 shows an acetone content of 131 ppm after one hour. For comparative purposes the same experiment is conducted with a dispersion of pure pyrogenic titanium dioxide (Degussa P25, BET surface area 50 $m^2/g$). 2303 ppm acetone are formed within the same period of time.

When the powder according to the invention is used, therefore, the photocatalytic activity is reduced to 5.7% of the activity of pure titanium dioxide.

Example 13

Sunscreen Preparations

A sunscreen preparation having 4 wt. % of the powder according to the invention in accordance with Example 3 is prepared using the formulation shown in Table 3.

TABLE 3

Sunscreen preparation containing the powder according to the invention from Example 3

| Phase | Constituent | Wt % |
|---|---|---|
| A | Isolan GI 34 | 3.0 |
|   | Castor oil | 1.2 |
|   | Tegesoft OP | 10.0 |
|   | Tegesoft Liquid | 5.0 |
|   | Glycerine 86% | 3.0 |
| B | Paracera W80 | 1.8 |
|   | Isohexadecane | 5.0 |
| C | Particles according to Example 3 | 4.0 |
| D | Magnesium sulfate | 0.5 |
|   | Completely demineralised water | 66.5 |

Phase A is heated to 70° C. in a mixer. Following melting at 80° C. on a magnetic heating plate, phase B is added to phase A. Phase C is stirred into the oil phase at approx. 300 rpm and under vacuum. Phase D is likewise heated to 70° C. and is added under vacuum to the mixture of A–C.

Obviously, numerous modifications and variations of the present invention are possible in light of the above teachings. It is therefore to be understood that within the scope of the appended claims, the invention may be practiced otherwise than as specifically described herein.

This application is based on German Patent Application Serial No. 101 63 938.4, filed on Dec. 22, 2001, and incorporated herein by reference.

The invention claimed is:

1. A silicon-titanium mixed oxide powder prepared by flame hydrolysis and comprising primary particles,
   wherein the ratio by weight of $SiO_2/TiO_2$ on the surface of the primary particles is greater than the ratio by weight of $SiO_2/TiO_2$ within the total primary particle; and
   wherein the ratio by weight of $SiO_2/TiO_2$ on the surface of the primary particles is from 0.01 to 99, in relation to the total $SiO_2/TiO_2$ of the primary particles.

2. The silicon-titanium mixed oxide powder of claim 1, wherein the ratio by weight of $SiO_2/TiO_2$ on the surface of the primary particles is from 0.05 to 4, in relation to the total $SiO_2/TiO_2$ of the primary particles.

3. The silicon-titanium mixed oxide powder of claim 1, wherein at a ratio by weight of $SiO_2/TiO_2$ on the surface of the primary particles of from 0.05 to 4, in relation to the total $SiO_2/TiO_2$ of the primary particles, the ratio by weight of $SiO_2/TiO_2$ on the surface of the primary particles assumes the value corresponding to the formula:

$$[SiO_2/TiO_2]_{surface}=9.3[SiO_2/TiO_2]_{total\ primary\ particle}^{1.24},$$

wherein the maximum absolute deviation of the ratio by weight of $[SiO_2/TiO_2]_{surface}$ from the indicated formula is 1.5.

4. The silicon-titanium mixed oxide powder of claim 1, wherein the BET surface area thereof is between 10 and 300 $m^2/g$.

5. The silicon-titanium mixed oxide powder of claim 1, wherein the primary particles form agglomerates.

6. A process for the preparation of the powder of claim 1, comprising:
   guiding separately into a reaction chamber of a burner a first stream consisting of a vaporous titanium dioxide precursor and oxygen or an oxygen-containing gas and hydrogen, and a second stream consisting of a vaporous silicon dioxide precursor and a carrier gas consisting of oxygen, an oxygen-containing gas and/or an inert gas,
   burning the first and second stream in the reaction chamber of the burner,
   cooling the solid mixed oxide powder and hot gases, and separating the gases from the solid;
   wherein titanium tetrachloride is introduced as the titanium dioxide precursor and silicon tetrachloride is introduced as the silicon dioxide precursor, in a manner such that the ratio by weight of $SiO_2/TiO_2$ on the surface of the primary particles is greater than the ratio by weight of $SiO_2/TiO_2$ within the total primary particle; and
   the ratio by weight of $SiO_2/TiO_2$ on the surface of the primary particles is from 0.01 to 99, in relation to the total $SiO_2/TiO_2$ of the primary particles.

7. The process of claim 6, wherein the stream consisting of silicon dioxide precursor and carrier gas is supplied at one or more positions in the reaction chamber.

8. The process of claim 6, wherein the mixed oxide powder is purified by a heat treatment by means of gases humidified with water vapor.

9. The process of claim 6, wherein inorganic and/or organic compounds are used as the titanium dioxide precursor and silicon dioxide precursor.

10. The process of claim 6, wherein titanium tetrachloride is introduced as the titanium dioxide precursor and silicon tetrachloride is introduced as the silicon dioxide precursor, in a manner such that the ratio by weight of $SiO_2/TiO_2$ on the surface of the primary particles becomes adjusted by the ratio by weight of $SiCl_4/TiCl_4$ corresponding to the formula:

$$[SiO_2/TiO_2]_{surface}=7.3[SiCl_4/TiCl_4]^{1.28},$$

with a 1.5 maximum absolute deviation of the ratio by weight of $[SiO_2/TiO_2]_{surface}$ from the formula, provided that the ratio by weight of $SiO_2/TiO_2$ on the surface of the primary particles in the subsequent powder is between 0.05 and 4, in relation to the total $SiO_2/TiO_2$ of the primary particles.

11. A sunscreen preparation comprising the powder of claim 1, in a proportion of between 0.01 and 25 wt. %, in relation to the quantity of the sunscreen preparation.

12. The sunscreen preparation of claim 11, which comprises at least one inorganic UV-absorbing pigment and/or at least one chemical UV filter.

13. The sunscreen preparation of claim 11, where the UV-absorbing pigment is selected from the group consisting of titanium dioxides, zinc oxides, aluminium oxides, iron oxides, silicon dioxide, silicates, cerium oxides, zirconium oxides, barium sulfate, and mixtures thereof.

14. The sunscreen preparation of claim 11, where the chemical UV filter is a water- or oil-soluble UVA or UVB filter.

15. The sunscreen preparation of claim 11, where the chemical UV filter is selected from the group consisting of sulfonic acid derivatives of benzophenones and benzimidazoles, derivatives of dibenzoyl methane, benzylidene camphors and derivatives thereof, derivatives of cinnamic acid and esters thereof, and esters of salicylic acid.

16. The sunscreen preparation of claim 11, which further comprises at least one member selected from the group consisting of solvents, cosmetic oils, emulsifiers, stabilisers, consistency regulators, vitamins, antioxidants, preservatives, dyes, and perfumes.

17. The sunscreen preparation of claim 11, which further comprises at least one member selected from the group consisting of water, monohydric or polyhydric alcohols, carbomers, cellulose derivatives, xanthan gum, waxes, bentones, and pyrogenic silicas.

18. A composition, comprising the silicon-titanium mixed oxide powder of claim 1 and a carrier.

19. The composition of claim 18, wherein the carrier is one or more members selected from the group consisting of solvents, cosmetic oils, and waxes.

20. The composition of claim 18, wherein the composition is a dispersion, a glass, a catalyst support, a toner, a silicone-containing composition, or a rubber-containing composition.

21. A method of preparing the composition of claim 18, which comprises:
   combining the silicon-titanium mixed oxide powder and the carrier.

22. A sunscreen preparation comprising the powder of claim 1, in a proportion of between 0.01 and 4 wt. %, in relation to the quantity of the sunscreen preparation.

23. A sunscreen preparation comprising the powder of claim 1, in a proportion of between 4 and 25 wt. %, in relation to the quantity of the sunscreen preparation.

* * * * *